(12) United States Patent
Cohen-Alloro et al.

(10) Patent No.: US 8,878,654 B2
(45) Date of Patent: *Nov. 4, 2014

(54) MEDICATION DISPENSER

(76) Inventors: Michael Cohen-Alloro, Tel-Aviv (IL);
Batami Sadan, Tel-Aviv (IL); Gilead Asseo, Kfar-MaAs (IL); Tomer Gofer, Yavne (IL)

(*) Notice: Subject to any disclaimer, the term of this patent is extended or adjusted under 35 U.S.C. 154(b) by 214 days.

This patent is subject to a terminal disclaimer.

(21) Appl. No.: 13/330,792

(22) Filed: Dec. 20, 2011

(65) Prior Publication Data

US 2012/0154120 A1 Jun. 21, 2012

Related U.S. Application Data

(63) Continuation of application No. 12/348,865, filed on Jan. 5, 2009, now Pat. No. 8,085,135, which is a continuation-in-part of application No. PCT/IL2007/000776, filed on Jun. 26, 2007.

(51) Int. Cl.
*A61J 1/03* (2006.01)
*A61J 7/04* (2006.01)
*G06F 19/00* (2011.01)

(52) U.S. Cl.
CPC .......... *A61J 7/0409* (2013.01); *G06F 19/3462* (2013.01); *A61J 2007/0436* (2013.01); *A61J 2007/0454* (2013.01); *A61J 2007/049* (2013.01); *A61J 2200/30* (2013.01)
USPC .............. 340/309.16; 340/571; 340/572.1; 340/693.6; 340/693.5; 340/10.1

(58) Field of Classification Search
None
See application file for complete search history.

(56) References Cited

U.S. PATENT DOCUMENTS

| | | | | |
|---|---|---|---|---|
| 4,660,991 A | * | 4/1987 | Simon | 368/10 |
| 4,695,954 A | | 9/1987 | Rose et al. | |
| 4,711,368 A | * | 12/1987 | Simons | 340/545.6 |
| 5,297,679 A | * | 3/1994 | Rondone et al. | 206/468 |
| 5,685,420 A | * | 11/1997 | Martin et al. | 206/5.1 |
| 5,930,145 A | | 7/1999 | Yuyama et al. | |
| 6,259,356 B1 | | 7/2001 | Tamaoki et al. | |
| 6,294,999 B1 | | 9/2001 | Yarin et al. | |

(Continued)

FOREIGN PATENT DOCUMENTS

| | | |
|---|---|---|
| EP | 1224903 | 7/2002 |
| EP | 1344514 | 9/2003 |

(Continued)

OTHER PUBLICATIONS

Communication Pursuant to Article 94(3) EPC Dated Feb. 2, 2011 From the European Patent Office Re. Application No. 07766807.7.

(Continued)

*Primary Examiner* — Julie Lieu

(57) ABSTRACT

Disclosed is a medication dispensing system comprising a container including at least two compartments each compartment including a cavity configured to contain at least one first medication, a covering over the cavity configured to break under pressure, and an elongate conductive element on at least a portion of the covering and configured sever upon breaking the covering. The medication dispensing system further includes one interrogator-readable RFID circuit operatively associated with the container and connected to the elongate conductive element of each of the at least two compartments, and one RFID circuit interrogator configured to interrogate the one RFID circuit and determine whether the elongate conductive element is severed on either on at least one of the at least two compartments.

40 Claims, 8 Drawing Sheets

(56) References Cited

U.S. PATENT DOCUMENTS

| | | | |
|---|---|---|---|
| 6,574,166 B2* | 6/2003 | Niemiec | 368/10 |
| 6,771,174 B2 | 8/2004 | Broas | |
| 7,369,919 B2 | 5/2008 | Vonk et al. | |
| 7,451,876 B2* | 11/2008 | Bossi et al. | 206/534 |
| 7,654,421 B2 | 2/2010 | Chan et al. | |
| 7,715,277 B2 | 5/2010 | de la Huerga | |
| 7,726,485 B2* | 6/2010 | Brollier | 206/534 |
| 7,828,147 B2* | 11/2010 | Caracciolo et al. | 206/530 |
| 8,181,772 B2* | 5/2012 | Short et al. | 206/1.5 |
| 8,525,677 B2* | 9/2013 | Scharfeld et al. | 340/572.8 |
| 2004/0206653 A1* | 10/2004 | Filion | 206/461 |
| 2005/0107914 A1 | 5/2005 | Engleson et al. | |
| 2005/0254348 A1 | 11/2005 | Niemiec et al. | |
| 2006/0058917 A1 | 3/2006 | Vonk et al. | |
| 2006/0202830 A1* | 9/2006 | Scharfeld et al. | 340/572.7 |
| 2006/0283748 A1* | 12/2006 | Daio et al. | 206/460 |
| 2007/0222613 A1 | 9/2007 | Fidelis et al. | |
| 2008/0059228 A1* | 3/2008 | Bossi et al. | 705/2 |
| 2008/0210701 A1 | 9/2008 | Cooper | |
| 2009/0301925 A1 | 12/2009 | Alloro et al. | |
| 2009/0307032 A1* | 12/2009 | Tribe et al. | 705/7 |
| 2009/0315702 A1 | 12/2009 | Cohen Alloro et al. | |
| 2013/0168405 A1* | 7/2013 | Yuyama et al. | 221/151 |
| 2013/0282163 A1* | 10/2013 | Brown, Arthur E. | 700/215 |

FOREIGN PATENT DOCUMENTS

| | | |
|---|---|---|
| EP | 1857090 | 11/2007 |
| GB | 2344194 | 5/2000 |
| JP | 2002-362652 | 12/2002 |
| JP | 2006-230860 | 9/2006 |
| WO | WO 2008/004212 | 1/2008 |

OTHER PUBLICATIONS

Communication Under Rule 71(3) EPC Dated Nov. 14, 2011 From the European Patent Office Re. Application No. 07766807.7.
Examination Report Under Section 18(3) Dated Nov. 23, 2009 From the Intellectual Property Office of the United Kingdom Re. Application No. GB0901306.1.
International Preliminary Report on Patentability Dated Mar. 17, 2009 From the International Bureau of WIPO Re.: Application No. PCT/IL2007/000776.
International Search Report Dated Jul. 9, 2008 From the International Searching Authority Re.: Application No. PCT/IL2007/00776.
Notice of Allowance Dated Aug. 23, 2011 From the US Patent and Trademark Office Re. U.S. Appl. No. 12/348,865
Official Action Dated Mar. 7, 2011 From the US Patent and Trademark Office Re. U.S. Appl. No. 12/348,865.
Official Action Dated Sep. 7, 2011 From the US Patent and Trademark Office Re. U.S. Appl. No. 12/307,574.
Official Action Dated Feb. 14, 2011 From the US Patent and Trademark Office Re. U.S. Appl. No. 12/307,574.
Patents Act 1977: Examination Report Under Section 18(3) Dated Dec. 7, 2010 From the Intellectual Property Office of the United Kingdom Re. Application No. 0901306.1.
Response Dated Jul. 7, 2011 to Official Action of Mar. 7, 2011 From the US Patent and Trademark Office Re. U.S. Appl. No. 12/348,865.
Response Dated Jul. 14, 2011 to Official Action of Feb. 14, 2011 From the US Patent and Trademark Office Re. U.S. Appl. No. 12/307,574.
Response Dated May 24, 2010 to Examination Report Under Section 18(3) of Nov. 23, 2009 From the Intellectual Property Office of the United Kingdom Re. Application No. GB0901306.1.
Response Dated May 26, 2010 to Communication Relating to Results of the Extended European Search Report of Jan. 7, 2010 From the European Patent Office Re.: Application No. 07766807.7.
Response Dated Jul. 27, 2011 to Communication Pursuant to Article 94(3) EPC of Feb. 2, 2011 From the European Patent Office Re. Application No. 07766807.7.
Response Dated Dec. 29, 2010 to Patents Act 1977: Examination Report Under Section 18(3) of Dec. 7, 2010 From the Intellectual Property Office of the United Kingdom Re. Application No. 0901306.1.
Supplementary European Search Report and the European Search Opinion Dated Jan. 7, 2010 From the European Patent Office Re.: Application No. 07766807.7.
Written Opinion Dated Jul. 9, 2008 From the International Searching Authority Re.: Application No. PCT/IL07/00776.
Inbar "Time Capsule—Electronic Pillbox", Japan Design Foundation Workshop, XP003025082, 6 P., Feb. 1, 2005.
Requisition by the Examiner Dated May 17, 2013 From the Canadian Intellectual Property Office Re. Application No. 2,691,965.
Requisition by the Examiner Dated Aug. 15, 2012 From the Canadian Intellectual Property Office Re. Application No. 2,691,965.
Requisition by the Examiner Dated Mar. 5, 2014 From the Canadian Intellectual Property Office Re. Application No. 2,691,965.
Invitation to Pay Additional Fees Dated Aug. 17, 2014 From the International Searching Authority Re. Application No. PCT/IL2014/050517.

* cited by examiner

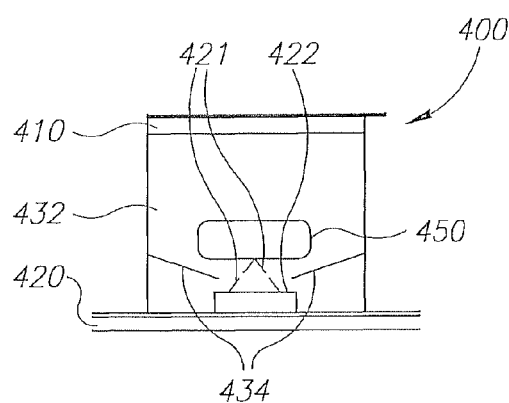
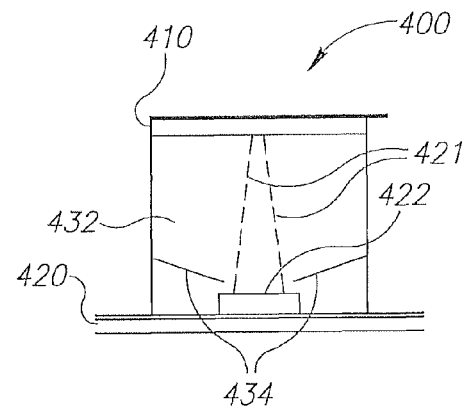
FIG.5A
FIG.5B
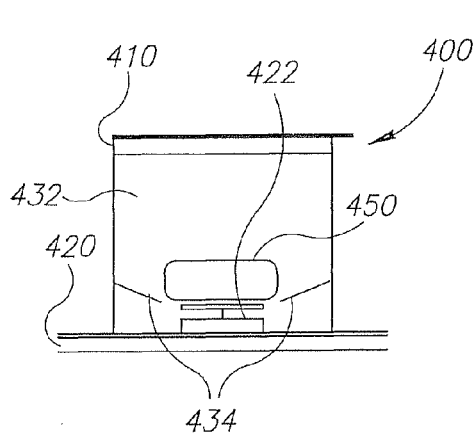
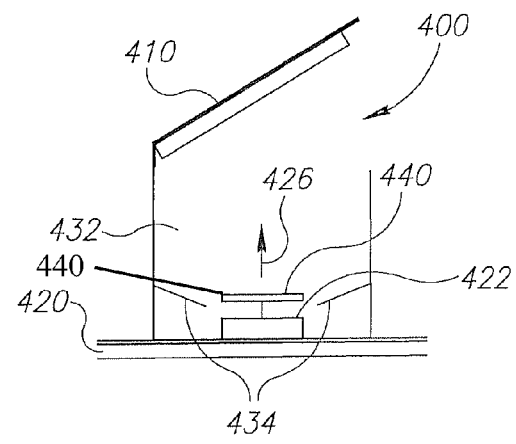
FIG.6A
FIG.6B

US 8,878,654 B2

MEDICATION DISPENSER

RELATED APPLICATIONS

This application is a continuation of U.S. patent application Ser. No. 12/348,865 filed on Jan. 5, 2009 now U.S. Pat. No. 8,085,135, which is a continuation-in-part (CIP) of PCT Patent Application No. PCT/IL2007/00776 filed on Jun. 26, 2007 which claims the benefit of priority from Israel Patent Application No. 176712 filed on Jul. 5, 2006.

The contents of all of the above applications are incorporated by reference as if fully set forth herein.

FIELD OF THE INVENTION

The present invention, in some embodiments thereof, relates to medicine dispensers having multiple compartments and, more particularly, but not exclusively, to multiple compartment medication dispensers that provide user guidance for serially opening the multiple compartments.

BACKGROUND OF THE INVENTION

Accurate Medication Dispensation

During the 20th century, increased life expectancy has been accompanied by the need for elderly persons to carefully follow specific medication regimens; for example before or after each of three daily meals are.

Most elderly wish to maintain an independent lifestyle without being institutionalized for as long as possible. Yet the failure to properly follow specific medication regimens was implicated in up to 40% of nursing home admissions in 2004.

Medication Dispensers

Medication Dispensers with audio, visual or vibratory reminders are known and include the following existing art, the disclosures of which are hereby incorporated herein by reference as if fully set forth herein:

U.S. Pat. No. 5,181,189 (Hafner);
U.S. Pat. No. 5,669,503 (Robin);
U.S. Pat. No. 5,915,558 (Girvetz);
U.S. Pat. No. 5,954,225 (Powe); and
U.S. Pat. No. 6,021,902 (Wu);
Medtime XL® marketed by e-Pill™ of Boston, Mass.; and EMMA® marketed by INRange Systems' of Altoona, Pa.

Electronic Tags

Electronically readable radio frequency identification (RFID) tags to ensure container integrity includes the following existing art, the disclosures of which are hereby incorporated herein by reference as if fully set forth herein:

U.S. Patent Application 20070069895 (Koh);
U.S. Patent Application 2005/0184871 (Coste);
U.S. Pat. No. 7,299,981 (Nickel et al); and
International Patent Application WO 2005/022443 (Atherton).

SUMMARY

According to an of some embodiments of the invention, there is provided a medication dispensing system comprising a container including at least two compartments each compartment including a cavity configured to contain at least one first medication, a covering over the cavity configured to break under pressure, an elongate conductive element on at least a portion of the covering and configured sever upon breaking the covering. The medication dispensing system further includes one interrogator-readable RFID circuit operatively associated with the container and connected to the elongate conductive element of each of the at least two compartments, and one RFID circuit interrogator configured to interrogate the one RFID circuit and determine whether the elongate conductive element is severed on either on at least one of the at least two compartments.

In some embodiments of the invention, the one interrogator-readable RFID circuit includes interrogator-readable data including a schedule for serially breaking the coverings on the at least two compartments.

In some embodiments of the invention, the one RFID circuit interrogator includes a user-cognitive output configured to provide a user with a cognitively-registerable signal according to the schedule for serially breaking the coverings on the at least two compartments.

In some embodiments of the invention, the user cognitively-registerable signal includes at least one signal including at least one of: an audio signal, a visual signal, and a vibratory signal.

In some embodiments of the invention, the at least the two compartments are removably connected to a base, the base including the one RFID circuit interrogator.

In some embodiments of the invention, the at least the two compartments are configured to be disposed following breaking the coverings on the at least two compartments.

In some embodiments of the invention, the at least two compartments are configured to be filled at a remote location.

In some embodiments of the invention, the at least two compartments are configured to be packaged in a package that facilitates shipment to a user via at least one of: a postal service, and a courier.

In some embodiments of the invention, the one interrogator-readable RFID circuit is configured to provide a user cognitively-registerable signal following breaking the coverings on the at least two compartments.

In some embodiments of the invention, the one interrogator-readable RFID circuit is configured to provide a user cognitively-registerable signal following at least one of: removal of a first set of the at least two compartments from the base, and replacement of the first set of the at least two compartments with a second set of at least two compartments.

In some embodiments of the invention, each of the base includes at least one audiovisual output associated with each of the at least two compartments, configured to provide an audiovisual signal to a according to the schedule for serially breaking the coverings on the at least two compartments.

In some embodiments of the invention, the at least one audiovisual output associated with each of the at least two compartments includes a light-emitting diode configured to emit light when the at least the two compartments are connected to the base.

In some embodiments of the invention, the schedule for serially breaking the coverings on the at least two compartments includes a medication consumption schedule.

In some embodiments of the invention, the one interrogator-readable RFID circuit includes data readable by the one RFID circuit interrogator and the base includes an audiovisual output configured to a provide a user cognitively-registerable audiovisual signal regarding at least one parameter associated with the medication consumption schedule.

In some embodiments of the invention, the at least one parameter associated with the medication consumption schedule includes at least one of: a name of user, a user dosage, an appearance of one of the at least one medication, a reaction symptom to the at least one medication requiring health provider notification, and at least one direction for consumption of the at least one medication with respect to food, including: take before food ingestion, take with food ingestion, and take after food ingestion.

In some embodiments of the invention, the base includes a wireless transponder connected to the one RFID circuit interrogator and configured to wirelessly transmit signals to a wireless remote transceiver, the transmitted signals including data related to at least one of: the schedule for serially breaking the coverings on the at least two compartments, the serially breaking of the coverings on the at least two compartments, removal of a first set of the at least two compartments from the base, and replacement of the first set of the at least two compartments with a second set of at least two compartments.

In some embodiments of the invention, the wireless remote transceiver is located at a health monitoring facility.

In some embodiments of the invention, the one interrogator-readable RFID circuit includes at least one chip including at least one code configured to be altered by a wireless signal originating at the health monitoring facility.

In some embodiments of the invention, the at least one code includes medication consumption data.

In some embodiments of the invention, at least one of: the wireless transponder, the wireless remote transceiver, the one RFID circuit interrogator, the at least one code, the user cognitively-registerable signal, and the user cognitively-registerable audiovisual signal, function autonomously and automatically.

According to a further aspect of the invention, there is provided a medication dispensing system including a base, a box configured to connect to the base, the box including at least two compartments, a first compartment configured to contain at least one medication and a second compartment configured to contain at least one medication. The system further including at least two sensors connected to the base and configured to align with at least a portion of the at least two compartments when the box is connected to the base, the at least two sensors configured to each provide at least one state-indicating signal that indicates a state of the compartment. The system further including a housing connected to the base, the housing including a wireless transponder connected to the at least two sensors and configured to wirelessly receive and transmit signals to a wireless remote health monitoring station, an audiovisual output connected to the at least two sensors, the audiovisual output configured to provide at least one audiovisual display responsive to the at least one state-indicating signal, and a power supply operatively associated with at least one of: the wireless transponder, the audiovisual output, and the at least two sensors.

In embodiments, the at least two compartments include a hatch and the at least one state-indicating signal indicates whether the hatch has been opened.

In embodiments, the at least one state-indicating signal indicates whether the at least one medication has been removed from at least one of the at least two compartments.

In embodiments, the at least two sensors are sensitive to the weight of the at least one medication.

In embodiments, the at least two sensors are sensitive to the presence of light and are positioned to be at least partially covered when at least one medication is contained within the compartment.

In embodiments, the at least two compartments are at least partially, at least one of transparent, and translucent.

In embodiments, the at least two compartments each include at least one aperture configured to transmit light waves.

In embodiments, the at least two sensors are wireless sensors providing radiant sensing beams from the group consisting of Ultrasound beams, laser beams, Split-light-beams, radar beams, infrared light beams and visible light beams.

In embodiments, the radiant sensing beams include reflected radiant sensing beams.

In embodiments, the box is configured to removably connect to the base.

In embodiments, the box is configured to be disposed following consumption of the at least one medication contained in the at least two compartments.

In embodiments, the housing includes a data reader and the box includes medication consumption data configured to be read by the data reader.

In embodiments, the medication consumption data includes a bar code and the data reader includes a bar code reader.

In embodiments, the medication consumption data includes at least one of the following: a name of user, a dosage a timing of dosage a medication appearance, and a medication reaction symptom requiring health provider notification.

In embodiments, the at least two compartments are configured to be filled at a remote location.

In embodiments, the at least two compartments are configured to packaged in a manner that facilitates shipment to a user via a postal service.

In embodiments, the at least two compartments are designed to be substantially easily attached to the base.

In embodiments, the at least two compartments are designed to be substantially easily removed from the base.

In embodiments, the system includes a remote medication filling location where the at least one medication compartment is filled.

In embodiments, the system includes at least two boxes, at least one first box and at least one second box, when the at least one first box is connected to the housing, the at least one second box is disconnected from the housing.

In embodiments, the at least one first box contains the at least one medication and the at least one second box is empty of medication.

In embodiments, the housing includes a clock display and clock set input, the audiovisual output is configured to display at least one of: an audiovisual alert confirming consumption of the at least one medication, an audiovisual alert to consume the at least one medication, an audiovisual alert to remove the at least one second box from the base, and an audiovisual alert to connect the at least one first box to the base.

In embodiments, the at least two sensors are attached to at least one of: the at least two compartments, and the base.

In embodiments, the housing includes a clock display and clock set input.

In embodiments, the at least two sensors are operative to sense and transmit a signal indicating that a hatch associated with the compartment is in at least one state of: open, and opening.

In embodiments, the at least two sensors are operative to sense and transmit a signal indicating that a hatch associated with the compartment is in at least one state of: open, and opening.

In embodiments, the wireless transponder includes a user activated inactive mode.

In embodiments, the transponder sends a wireless signal that the wireless transponder is in the inactive mode to the remote health monitoring station.

In embodiments, the at least one audiovisual output on the housing includes at least one of: an LED display, a liquid crystal display, a twisted crystal display, and a phosphor display.

In embodiments, the system includes a remote health monitoring station is configured to wirelessly transmit the medication consumption data to the wireless transponder.

In embodiments, the remote health monitoring station is configured to wirelessly update the medication consumption data.

In embodiments, the audiovisual output is configured to provide at least one signal based upon at least one of: the medication consumption data and the state of the at least two compartments. In embodiments, 30 the at least two sensors are operative to sense and transmit a signal indicating that the at least one medication has been accessed at an improper time, based upon the medication consumption data.

In embodiments, the at least two sensors are configured to transmit a signal indicating that a wrong compartment has been accessed based upon the medication consumption data.

In embodiments, the wireless transponder is configured to transmit wireless signals to the remote health monitoring station in the absence of a change in compartment state according to the consumption data within a programmed period of time.

In embodiments, the remote health monitoring station is configured to communicate with the transponder in the absence of a change in compartment state within a programmed period of time. In embodiments, the communication includes providing at least one display transmitted by the remote health monitoring station via the audiovisual display.

In embodiments, the remote health monitoring station is configured to additionally transmit a message to a user through at least one of: a cellular telephone, and a hard-wired telephone.

In embodiments, the remote health monitoring station is configured to issue a directive to contact a user, the directive being transmitted to at least one of: an acquaintance of the user, a medical person, and an emergency response system.

In embodiments, the at least two compartments are configured to operate in conjunction with the audiovisual output on least one of: two or more times during a day, and two or more days.

In embodiments, the power source includes at least one battery. In embodiments, the housing includes at least one battery. In embodiments, the at least one battery is rechargeable. In embodiments, the power source includes a DC current, supplied by an AC/DC transformer.

In embodiments, the housing is configured to include at least one rechargeable battery configured to be recharged via the DC current. In embodiments, the housing is configured to include the AC/DC transformer and further includes an AC input receptacle.

In embodiments, the AC/DC transformer is located outside the housing and the housing further includes a DC input receptacle.

In embodiments, the AC/DC transformer is part of a USB system and the housing further includes a USB input receptacle.

In embodiments, the transponder is configured to receive an SMS messaging protocol and the at least one audiovisual output is configured to display the SMS protocol.

In embodiments, the remote health monitoring station includes an SMSC.

In embodiments, the system includes a local wireless relay station configured to wirelessly receive the transponder signals and to receive and transmit signals to the wireless remote health monitoring station.

In embodiments, the local wireless relay station includes a cellular telephone chip.

In embodiments, the local wireless relay station communicates with the transponder using at least one of Bluetooth communication, RF and infrared communication.

In embodiments, the remote health monitoring station further includes a Web server for communication through a Web-based function.

In embodiments, the communication through the Web-based function includes an analysis by a medical professional.

In embodiments, the system includes at least one integrated chip imprinted with at least two of: a circuit of the at least two sensors, a circuit of the at least one audiovisual output, and a circuit of the wireless transponder.

In embodiments, at least one of the at least two compartments is about 25 millimeters on each of the X and Y axes.

In embodiments, at least one of aid at least two compartments is about at least one of 10 millimeters, 15 millimeters, and 20 millimeters on the X and Y axes.

In embodiments, at least one of the at least two compartments is no more than at least one of about 30 millimeters, 40 millimeters, and 50 millimeters on the X and Y axes.

In embodiments, at least one of the at least two compartments have different measurements along the X axis than along the Y axis.

In embodiments, at least one of the at least two compartments have polygonal shapes on the X and Y axes.

In embodiments, at least one of the at least two compartments has at least one shape of: triangular, rectangular, and hexagonal, on the X and Y axes.

In embodiments, at least one of the at least two compartments have a curved shape on the X and Y axes.

In embodiments, at least one of the at least two compartments is about 25 millimeters deep on the Z axis.

In embodiments, at least one of the at least two compartments is at least one of about 10 millimeters, 15 millimeters, and 20 millimeters deep on the Z axis.

In embodiments, at least one of the at least two compartments is no more than about 30 millimeters, 40 millimeters, or even 50 millimeters deep on Z axis.

In embodiments, at least one of the box and the base include a material selected from the group consisting of: polyethylene, polyvinyl chloride, polyurethane, nylon and a biocompatible polymer fiber.

In embodiments, at least one of the box and the base include a material selected from the group consisting of: metals, synthetic biostable polymer, a natural polymer, and an inorganic material.

In embodiments, the biostable polymer includes a material from the group consisting of: a polyolefin, a polyurethane, a fluorinated polyolefin, a chlorinated polyolefin, a polyamide, an acrylate polymer, an acrylamide polymer, a vinyl polymer, a polyacetal, a polycarbonate, a polyether, a polyester, an aromatic polyester, a polysulfone, and a silicone rubber.

In embodiments, the natural polymer includes a material from the group consisting of: a polyolefin, a polyurethane, a Mylar, a silicone, and a fluorinated polyolefin.

According to another aspect of the invention, there is provided a method for monitoring consumption of medication from a medication box, the method including: filling at least two medication compartments on a first medication box with medication, sending the first medication box to a user connecting the at least two medication compartments to at least two medication sensor transponders receiving signals from the at least two medication sensor transponders at a central station, and communicating with the user based upon the signals received from the at least two medication sensor transponders.

The method wherein the medication box is disposable and the method further includes: disposing of the first medication box upon consumption of the medication, filling at least two medication compartments on a first medication box with medication, sending the first medication box to a user, and connecting the at least two medication compartments to at least two medication sensor transponders.

According to still another aspect of the invention, there is provided an autonomous and automatic medication dispensing system that works in conjunction with a remote health monitoring station, the system including a box including at least two compartments having a compartment-securing hatch, the at least two compartments configured to contain at least one medication, at least two sensors operatively associated with the at least two compartments and configured to provide at least one state-indicating signal that indicates a state of the compartment, a housing configured to connect to the at least one medication compartment, the housing including several items, including a CPU connected to the at least two sensors and configured to provide at least one CPU audiovisual output signal responsive to the at least one state-indicating signal a wireless transponder connected to the CPU and configured to wirelessly receive and transmit signals to a wireless remote health monitoring station an audiovisual output connected to the CPU and to the wireless transponder, the output configured to provide at least one audiovisual display responsive to at least one of: the CPU audiovisual output signal, and the wireless transponder, a power source operatively associated with at least one of the items included in the housing a wireless monitoring device that monitors a condition of a user, the monitoring device configured to wirelessly receive and transmit signals to a wireless remote health monitoring station, a wireless remote health monitoring station configured to receive and transmit wireless signals to the wireless transponder and the wireless monitoring device.

In embodiments, the at least two sensors are attached to at least one of: the at least two compartments, and the housing.

In embodiments, the housing includes a clock display and clock set input.

In embodiments, the at least two sensors are operative to sense and transmit a signal indicating that a hatch associated with the compartment is in at least one state of: open, and opening.

In embodiments, the at least two sensors are operative to sense and transmit a signal indicating that a hatch associated with the compartment is in at least one state of: open, and opening.

In embodiments, the CPU includes a user activated inactive mode.

In embodiments, the transponder sends a wireless signal that the CPU is in the inactive mode to the remote health monitoring station.

In embodiments, the at least one audiovisual output on the housing includes at least one of: an LED display, a liquid crystal display, a twisted crystal display, and a phosphor display.

In embodiments, the CPU includes medication consumption data, the data including at least one of the following a name of user, a dosage, a timing of dosage, a medication appearance, and a medication reaction symptom requiring health provider notification.

In embodiments, the audiovisual output provides a display until the hatch state is opened according to the consumption data.

In embodiments, the remote health monitoring station is configured to wirelessly transmit the medication consumption data to the wireless transponder.

In embodiments, the remote health monitoring station is configured to wirelessly update the medication consumption data.

In embodiments, the audiovisual output is configured to provide at least one signal based upon at least one of: the medication consumption data, and the state of the compartment-securing hatch.

In embodiments, 82 the at least two sensors are operative to sense and transmit a signal indicating that the medication has been accessed at an improper time, based upon the medication consumption data.

In embodiments, the at least one medication compartment includes at least two medication compartments, each compartment operatively associated with at least two sensors.

In embodiments, the at least two sensors are configured to transmit a signal indicating that a wrong compartment has been accessed based upon the medication consumption data.

In embodiments, the wireless transponder is configured to transmit wireless signals to the remote health monitoring station in the absence of a change in compartment state according to the consumption data within a programmed period of time.

In embodiments, the remote health monitoring station is configured to communicate with the transponder in the absence of a change in compartment state within a programmed period of time. In embodiments, the communication includes providing at least one display transmitted by the remote health monitoring station via the audiovisual display.

In embodiments, the remote health monitoring station is configured to additionally transmit a message to a user through at least one of: a cellular telephone, and a hard-wired telephone.

In embodiments, the remote health monitoring station is configured to issue a directive to contact a user, the directive being transmitted to at least one of: an acquaintance of the user, a medical person, and an emergency response system.

In embodiments, the at least two compartments are configured to operate in conjunction with the audiovisual output on least one of: two or more times during a day, and two or more days. In embodiments, the power source includes at least one battery. In embodiments, the housing includes at least one battery. In embodiments, the at least one battery is rechargeable. In embodiments, the power source includes a DC current, supplied by an AC/DC transformer.

In embodiments, the housing is configured to include at least one rechargeable battery configured to be recharged via the DC current. In embodiments, the housing is configured to include the AC/DC transformer and further includes an AC input receptacle. In embodiments, the AC/DC transformer is located outside the housing and the housing further includes a DC input receptacle.

In embodiments, the AC/DC transformer is part of a USB system and the housing further includes a USB input receptacle.

In embodiments, the transponder is configured to receive an SMS messaging protocol and the at least one audiovisual output is configured to display the SMS protocol.

In embodiments, the remote health monitoring station includes an SMSC.

In embodiments, the system includes a local wireless relay station configured to wirelessly receive the transponder signals and to receive and transmit signals to the wireless remote health monitoring station.

In embodiments, the local wireless relay station includes a cellular telephone chip.

In embodiments, the local wireless relay station communicates with the transponder using at least one of Bluetooth communication, RF and infra-red communication.

In embodiments, the remote health monitoring station further includes a Web server for communication through a Web-based function.

In embodiments, the communication through the Web-based function includes an analysis by a medical professional.

In embodiments, the system includes at least one integrated chip imprinted with at least two of: a circuit of the at least two sensors, a circuit of the at least one audiovisual output, and a circuit of the wireless transponder.

According to a further aspect of the invention, there is provided a method for providing medication according to a preset schedule in conjunction with a user monitoring device, the method including: providing a medication dispenser to a user, the dispenser having at least two compartments, connecting compartment monitors to the at least two compartments, the monitor configured to monitor a state of the at least two compartments and provide digital signals with respect to the state of the at least two compartments providing the digital signals to a wireless transponder configuring the transponder to wirelessly communicate the signals to a wireless remote health monitoring station, The method further including locating proximate to the medication dispenser a wireless user monitoring device that monitors and provides digital signals on a condition of the user, and configuring the user monitoring device to wirelessly communicate the user monitoring signals with the wireless remote health monitoring station.

The method further includes providing alerts pertaining to a user condition communicated by the user monitor, and a state of aid at least two compartments.

The method further including integrating an audiovisual output with the dispenser and providing an audiovisual signal responsive to a state of the at least two compartments.

The method further includes providing an audiovisual signal via the audiovisual output, the signal being responsive to the wireless remote health monitoring station.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings.

With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1 shows a schematic view of a medication dispensing system in conjunction with a consumer health sensor, according to embodiments of the invention;

FIGS. 2-6B show alternative embodiments of the medication dispensing system shown in FIG. 1, according to embodiments of the invention;

FIG. 7 shows a Flowchart of a medication dispensing, according to embodiments of the invention.

FIG. 8 shows a schematic diagram of an RFID transponder tag and medication compartment, according to embodiments of the invention; and FIG. 9, shows an RFID medication dispenser and an exploded view of a disposable medicine insert, according to embodiments of the invention.

DESCRIPTION OF EMBODIMENTS OF THE INVENTION

Figure 1:
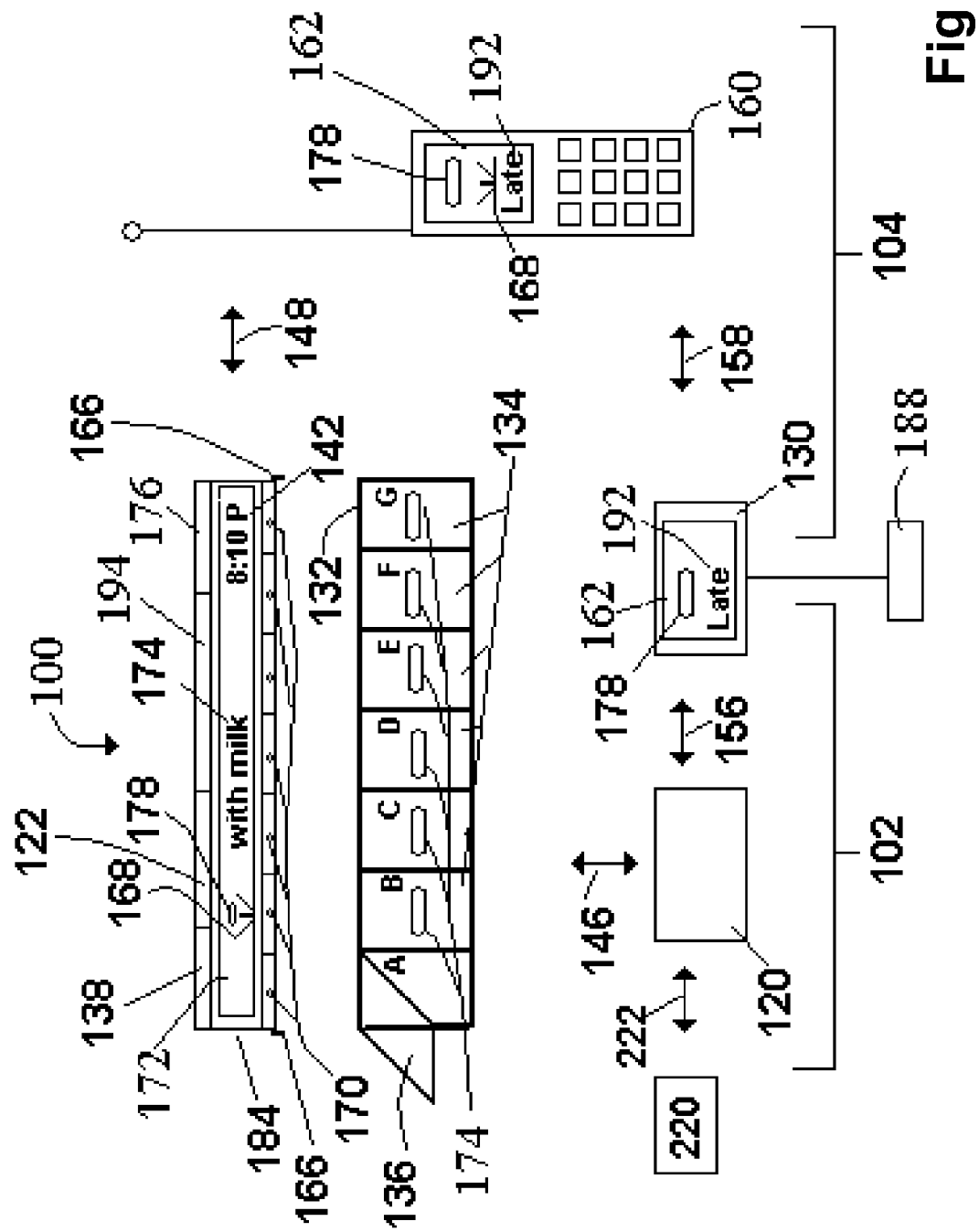

The present invention, in some embodiments thereof, relates to medicine dispensers having multiple compartments and, more particularly, but not exclusively, to multiple compartment medication dispensers that provide user guidance for serially opening the multiple compartments.

The principles and uses of the teachings of the present invention may be better understood with reference to the accompanying description, Figures and examples. In the Figures, like reference numerals refer to like parts throughout.

Before explaining at least one embodiment of the invention in detail, it is to be understood that the invention is not limited in its application to the details set forth herein. The invention can be implemented with other embodiments and can be practiced or carried out in various ways.

It is also understood that the phraseology and terminology employed herein is for descriptive purpose and should not be regarded as limiting.

Generally, the nomenclature used herein and the laboratory procedures utilized in the present invention include techniques from the fields of biology, engineering, material sciences, medicine and physics. Such techniques are thoroughly explained in the literature.

Unless otherwise defined, all technical and scientific terms used herein have the same meaning as commonly understood by one of ordinary skill in the art to which the invention belongs. In addition, the descriptions, materials, methods, and examples are illustrative only and not intended to be limiting. Methods and materials similar or equivalent to those described herein can be used in the practice or testing of the present invention.

As used herein, the terms "comprising" and "including" or grammatical variants thereof are to be taken as specifying the stated features, integers, steps or components but do not preclude the addition of one or more additional features, integers, steps, components or groups thereof. This term encompasses the terms "consisting of" and "consisting essentially of".

The phrase "consisting essentially of" or grammatical variants thereof when used herein are to be taken as specifying the stated features, integers, steps or components but do not preclude the addition of one or more additional features, integers, steps, components or groups thereof but only if the additional features, integers, steps, components or groups thereof do not materially alter the basic and novel characteristics of the claimed composition, device or method.

As used herein, "a" or "an" mean "at least one" or "one or more". The use of the phrase "one or more" herein does not alter this intended meaning of "a" or "an".

The term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts. Implementation of the methods of the present invention involves performing or completing selected tasks or steps manually, automatically, or a combination thereof.

Medication Dispensing System

FIG. 1 shows a schematic view of a medication reminder and dispensing system 100. System 100 includes an electronic monitoring unit 184 having clips 166 that removably connect to a medication compartment 132. Compartment 132 includes medication berths 134A-134G containing medication 174B-174G. Hatches 136B-136G are in the closed positions.

In an exemplary embodiment, monitoring unit 184 includes a Computerized Processing Unit (CPU) 138 that includes a medication consumption data module. CPU 138 typically includes medication data related to, inter alia:
a) name of user;
b) dosage;
c) medication appearance; and
d) medication reaction symptoms requiring health provider notification.

CPU 138 is connected to an audiovisual display 172, powered by a power system 194, configured to visually demonstrate an image 178 of one or more medications. CPU 138 provides an audiovisual indication 168 that indicates which berth 134 to open and, optionally, a message 174 regarding consumption conditions, for example to consume "with milk".

The term "conditions", as used herein, refers to general directions for taking medication, including but not limited to, "take with food," and/or is optionally based upon consumer medical history, for example, warning a diabetic to check blood sugar prior to taking a dose of insulin.

Additionally, display 172 includes a clock 142 that is synchronized with CPU 138 and optionally flashes a set period of time prior to consumption of medication 174. In the assembled position, compartment 132 connects to electronic unit 184 with clips 166, thereby aligning hatches 136A-136G with sensors 170A-170G.

Hatch Sensors

Upon opening hatch 136A, shown in the open position, a hatch sensor 170A registers the opening and transmits a signal to CPU 138. Should a consumer fail to open hatch 174A within a given period in conjunction following a signal to consume a medication, audiovisual display 172 provides one or more of a variety of demonstrations including, inter alia, sounds, vibrations, visual flashes and moving images.

Optionally, hatch sensor 170A senses when hatch 136A is opened partially, for example, in a manner that does not allow a user access to medication 174A. In such cases, hatch sensor 170A does not provide a hatch "open" signal, but either a null signal or a signal that hatch 136A has been improperly opened. CPU 138, in turn, signals audiovisual display 172 to provide a display that indicates that medication hatch 136A must be reopened and medication 174A removed.

Should the user open wrong hatch 170B, hatch sensor 170B registers opening and audiovisual display 172 immediately provides one or more of a variety of demonstrations noted above to direct the user to close wrong hatch 170B and, instead, open correct hatch 170A.

The term "medication" as used herein is intended to include any vitamin, mineral, substance or medicine, including tablets, capsules, powders and liquids of prescription and non-prescription items. In embodiments, aerosols, powders and liquids are packaged in easily opened discrete packages and dispensed from system 100.

Compartment Connection Memory

In an exemplary embodiment, system 100 includes detachment sensor 122 that senses when compartment 132 has been detached from unit 184 for example when the user wishes to take a walk without the necessity of carrying unit 172. Detachment sensor is programmed to communicate the detachment of clips 166 and to communicate to CPU 138 that a lack of movement of hatches 136 does not indicate non-compliance.

Upon the return of the user and the hook up of unit 172 with compartment 132, detachment sensor 122 updates CPU 138 on the state of dispenser, for example, that in a certain period of time, hatch 134E should be opened by the user.

Optionally, unit 184 includes sensors that sense when clips 166 are properly aligned with compartment 132 upon connection of compartment 132. Should clips 166 be, for example, in partial connection with compartment 174 that misaligns hatch sensors 170, CPU 138 provides an appropriate alert on audiovisual display 172 to remind the user to realign compartment 132 with unit 184.

Wireless Communication

In an exemplary embodiment, system 100 includes a unit transponder 176 that communicates wirelessly 146 with a local wireless relay 120, which, for example, is located within several to several tens of meters of unit 184 and communicates with system 100 via wireless signals 146.

Local wireless relay 120, in turn, communicates wirelessly 156 with a central processing data bank 188. In an exemplary embodiment, central data bank 188 is operatively associated with a health data bank 162 that is in wireless communication with at least one user monitor device 220, as defined below. Optionally, central processing data bank 188 communicates directly with unit transponder 176, thereby bypassing wireless relay 120; a user option provided, for example, to a user who is active and periodically takes unit 184 and compartment 132 out of range of wireless relay 120.

In an exemplary embodiment, data bank 188 is programmed by an operator and, thereafter, system 100 functions to ensure that the user has, in fact, complied with a given medication consumption schedule without intervention of the operator. In embodiments, system 100 and data bank 188 function in an autonomic and autonomous fashion, and initiate actions with respect to user non-compliance. Additionally or alternatively, system 100 and data bank 188 function under the observation of an operator as explained below.

In an embodiment, transponder 176 communicates wirelessly 248 with a cell phone 160 in a closed loop system so that phone 160 provides additional back-up to remind the user to take medication 174. Optionally, communication between transponder 176 and cell phone 160 and reminding a user to consume medication 174 occurs automatically and autonomically in a closed loop.

Automatically is defined as having a self-acting or self-regulating mechanism. Autonomically is defined as responding independently. (Miriam Webster Dictionary)

In embodiments, CPU 138 additionally provides messages to the consumer via cell phone 160 using least one of a SMS (Short Message Service) or MMS (Multi Media Service), or via Internet based messaging (such as in cellular telephones operating in GPRS networks).

The many means of initiating and maintaining closed loop reminders to the user via cell phone 160 are well known to those familiar with the art.

In embodiments, CPU 138 optionally provides messages to the consumer via WiMax, WiFi, Zigbee, USB wireless communication; the many wireless systems for communication being well known to those familiar with the art.

Remote Medication Preparation

In embodiments, hoppers 134 are loaded with medication 174 by a person familiar to the consumer at the consumer location, for example, in a private home.

In other embodiments, filling of system 100 with medication is in conjunction with central processing data bank 188. For example, hoppers 134 are loaded with medication 174 in proximity to data bank 188 and shipped to the user.

Alternatively, system 100 communicates to locations outside of system 100, for example, to a telephone located at a local pharmacy where hoppers 134 are loaded with medication 174. As changes in dosage and/or new information on drug interactions become available on medication 174, the pharmacy is updated via a telephone. In this fashion, reminders to take medication 174, programming of CPU 138 and filling of compartment 132 are automatic and autonomic.

In embodiments, computer chips, not shown, are optionally provided to the user or the pharmacist and inserted into system 100 to interact with CPU 138, thereby updating system 100 on, inter alia, the medical state of the user, medication scheduling and/or changes in dosage.

Medication System Alerts

In an exemplary alternative embodiment central data bank 188 includes a screen 162 that provides a supervisor with a visual alert 192 that notifies the supervisor that medication 174 has not been consumed within a certain period of time.

In embodiments, after waiting a period of time for the user to respond to indicator 168, the operator initiates an inquiry to the user telephonically through cell phone 160 and/or a designated caretaker. With personal contact, visual inspection ensures that the user has not suffered an untoward health condition, for example a heart attack.

In an exemplary embodiment, unit 184 communicates wirelessly 248 with a cellular phone 160 that is carried by the user. If the user fails to take medication 174, a signal is transmitted wirelessly 148 so that phone 160 provides indicator 168 and or messages 192 to reinforce audiovisual display 172.

In an exemplary embodiment, following a given number of wireless communications 148, a wireless signal 158 or 146 is transmitted to central data bank 188 and an inquiry is made of the user as noted above.

User Monitoring

Referring to component system 102, system 100 optionally includes at least one user monitor device 220 that is operatively associated with wireless relay 120, for example, through a wireless signal 222.

User monitor device 220 typically receives a user parameter, for example, whether the user is in distress, has a high pulse rate, or has fainted. User monitor device 220 then communicates the parameter to local wireless relay 120 via wireless signal 222. The sensed parameter is then passed on to a central data bank 188 where the parameter is analyzed and appropriate action is initiated, either by central data bank 188 or via a supervisor associated with a health monitoring agency as noted below.

As used herein the term "central processing data bank 188" refers to any data bank including medication consumption information and/or user parameters with respect to user monitoring device 220.

Health Monitoring Service

By way of example only, the human operator is part of a health alert system, known in the art, for example "Lifeline", a subsidiary of Philips Corporation. The devices offered by Lifeline include a personal health alert button that is worn around the neck, wrist, or another body part. In embodiments, the use presses the alert button when faced with symptoms of an apparent looming medical emergency. All information regarding the operation of "Lifeline" is hereby included in its entirety as if fully written herein.

In an exemplary embodiment, the human operator optionally assesses the user's current medical condition from the received information based upon user medical history, which is stored in remote central data bank 188.

In some embodiments, central data bank 188 acts as gateway, only alerting the operator when a parameter passes normal limits as indicated in the patient history. In other embodiments, for example, when device 220 is used in conjunction with an ECG monitor, a monitor 130 continually provides an ECG signal for observation by the operator.

In some embodiments, user monitor device 220 includes a wrist-mounted sensor that, for example, senses pulse rate. Alternatively, user monitor device 220 is mounted, worn, carried or otherwise in contact with substantially any part of the body or in close proximity to the user body. As another non-limiting example, user monitor device 220 is optionally in the form of a necklace for being worn at the neck of the subject.

User monitor device 220 optionally includes a panic input that is activated by a user, alternatively or in addition, to sensor 220. In embodiments, panic button monitor device 220 is mounted on and/or connected to electronic monitoring unit 184.

Examples of parameters that are sensed by user monitor device 220 and or interpreted by central data bank 188 based upon information supplied by user monitor device, optionally include, inter alia: heart rate; heart rate variability; breathing rate; arrhythmia of the heart, general rhythm and functioning of the heart; blood pressure; presence of abnormal body movements such as convulsions for example; body position; general body movements; body temperature; presence and level of sweat; oxygen pressure in the blood.

In embodiments, central data bank 188 supports manual and/or automatic collection of the one parameter; and is able to execute one or more instructions for extracting medical information about the user when such measurements relate, for example, to a physiologic parameter.

In some embodiments, a human operator, optionally a trained medical person sees this information on central data bank monitor 130 and talks to the patient using cellular telephone 160 that communicates with the user either directly or through audiovisual display 172.

Additionally or alternatively, the operator receives and/or communicates with the user or other locations via a LAN (local area network) connection or an Internet connection. In embodiments, the operator communicates with the user via cell phone 160 using least one of a SMS or MMS, or electronic mail such as an e-mail message or facsimile, or Internet based messaging (such as in cellular telephones operating in GPRS (General Packet Radio Service) networks.

The many means of maintaining contact with the user while medical personnel proceed to the home of the user; and maintaining communication with medical personnel are well known to those familiar with the art.

In some embodiments, cell phone 160 includes an add-on video camera, such as in the case of 3G (third generation) cellular telephones, that enables a visual and audio conversation is made between the call center operator and the user.

In embodiments, communication with system 100 includes an add-on to cell phone 160 with standard access, for example Bluetooth, IEEE 802.11 protocol or IRDA (Infrared Data Association).

Optionally, an alarm signal that communicates user distress is transmitted to family members, and/or caregiver, for example, by sending an SMS message to their cellular telephone or by a voice message.

In some embodiments, wireless link 248 between system 100 and cell phone 160 uses Home RF protocol or alternatively any other proprietary protocol using a RF link, any type of wireless infrared, or any other radio frequency protocol communication link.

In embodiments, local wireless relay 120 is located in proximity to unit 100, is connected to a standard power supply and has a broadcast range sufficient to communicate with data bank 188. In embodiments, local transponder performs additional duties in addition to monitoring system 100, for example providing monitoring of oxygen consumption in sleep apnea, and/or monitoring blood pressure.

Figure 2:
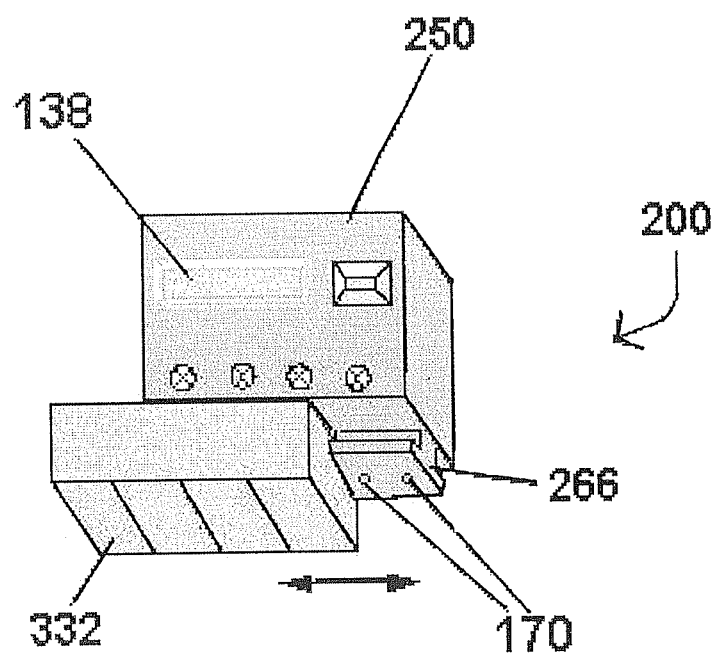

System 200:

FIG. 2 shows an alternative embodiment for medication reminder and dispensing, comprising system 200 in which a disposable box including multiple compartments 132 slides onto a transverse support 266 including sensors 170.

System 300

Figure 3:
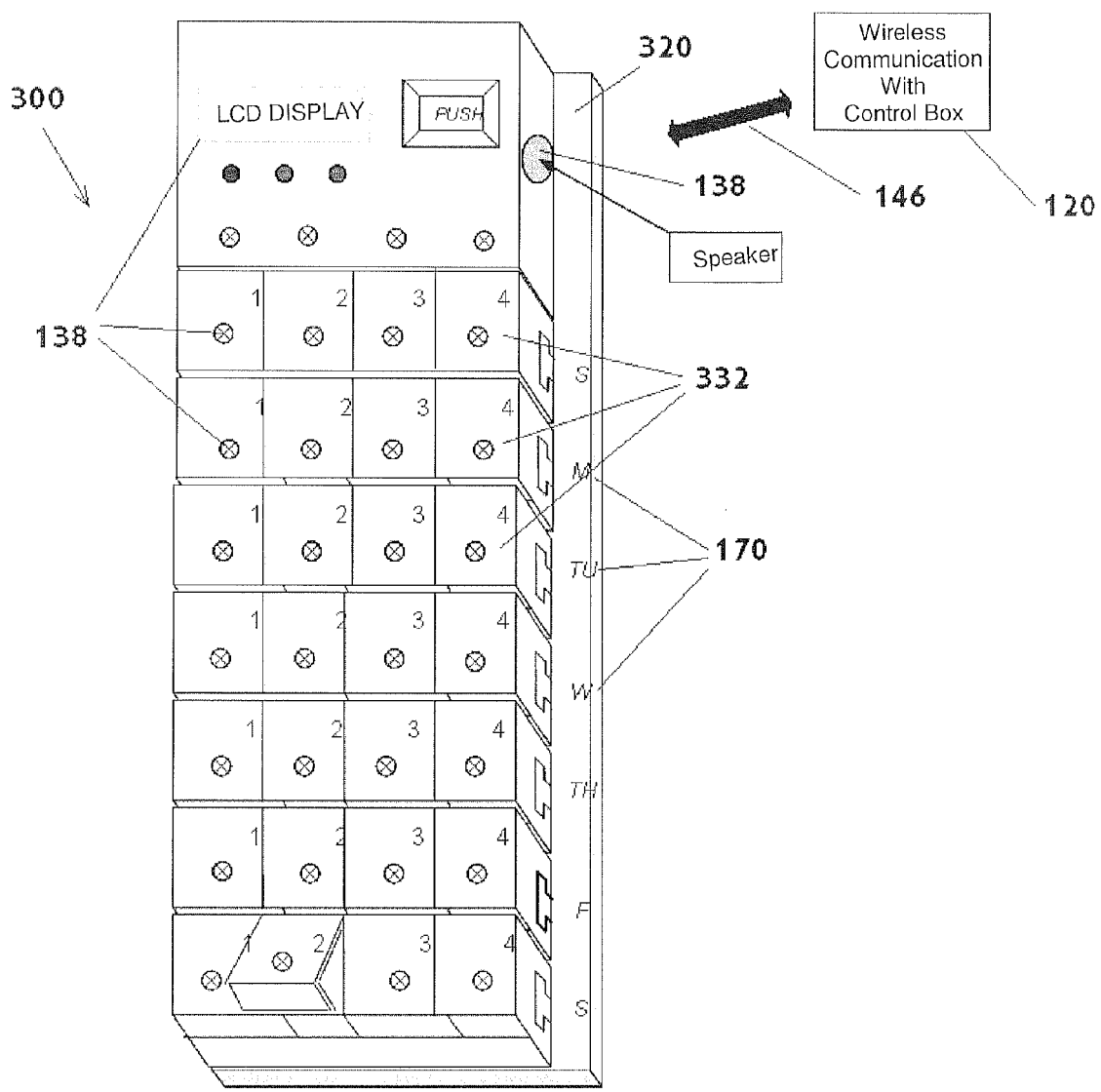

FIG. 3 shows an alternative embodiment for medication reminder and dispensing, comprising system 300 that includes a base 320 to which multiple compartments 332 attach. Compartments 332 interconnect via transverse supports 266. In an exemplary embodiment, sensors 170 on base 320 are operatively associated with compartments 332.

System 400

Figure 4:
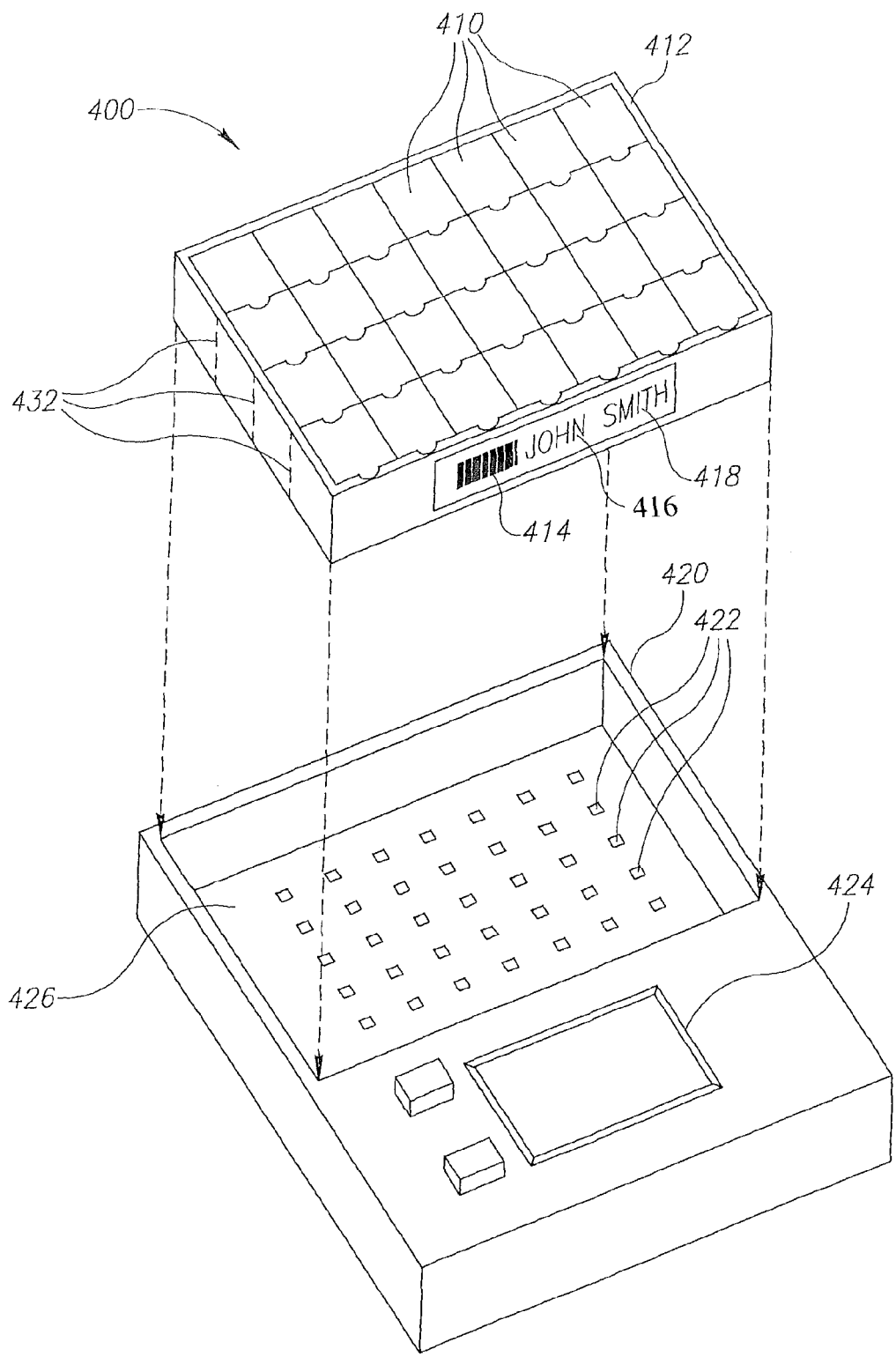

FIG. 4 shows an alternative embodiment of the medication reminder and dispensing system of FIG. 3, comprising system 400 that includes a disposable box 412 with hatches 410 on medication compartments 432. Disposable box 412 is typically filled at a central facility and shipped to a user.

The user loads disposable box 412 on base unit 420 and base unit reads a bar code 414 on an identification label 416 which optionally includes user readable information 418, for example the name of the user.

Bar code 414 includes medication dispensing information, a first portion of which is displayed on a display 424 and a second portion of which directs box 400 to communicate with the central station regarding patient compliance. Additionally, base unit 420 includes a base board 426 having an array of sensors 422.

In alternative embodiments, identification label 416 includes a radio frequency (RF) identification tag and base unit 420 includes an RF reader which is displayed on display 424 and at the central station.

While system 400 is shown with 28 compartments 432, system 400 optionally has at least about five, 10 or 12 compartments 432. Alternatively, system 400 has no more than about 30, 50, 100 or even 300 compartments 432, each compartment 432 having one or more sensors 422 on baseboard 426.

FIG. 5A shows one embodiment of system 400 in which compartment 432 includes a curved floor 434 that directs medication 450 to sit over a sensor 422. Sensor 422 emits wireless reflecting radiant waves 421 that reflect off a medication 450, with a short reflection time indicating the presence of pill 450.

FIG. 5B shows radiant waves 421 reflecting off hatch 410 in the absence of medication 450, with the longer reflection time indicating that compartment 432 has been emptied of medication 450. Additionally or alternatively, sensors 422 are optionally configured to determine the position of hatch 410, as explained above. Sensor 422 is optionally any variety of radiant wave transceivers that determine distance from any one of several reflected wireless waves 421, as described in the following patents, the entirety of which are incorporated herein by reference as if fully set forth herein:

i) U.S. Pat. No. 6,181,645 (Li), which teaches Ultrasound waves 132;
ii) U.S. Pat. No. 5,266,955 (Izumi, et al), which teaches waves comprising a laser beam 132;
iii) U.S. Pat. No. 4,833,469 (David), which teaches a variety of sensors including, inter alia, optical image Split-light wave beams; and radar (Radio Detecting And Ranging) waves employing a short pulse of electromagnetic radiation;
iv) U.S. Pat. No. 4,165,936 (Eisenring et al), which teaches dual infrared light waves 132; and
v) U.S. Pat. No. 5,214,293 (MacNiel), which teaches a reflecting visible light wave.

Alternatively, sensor 422 is light sensor and the presence of medication 450 over sensor 422, light is blocked, thereby indicating the presence of medication 450. Upon removal of medication 450, the presence of ambient light signifies that medication 450 has been removed from compartment 432.

In embodiments, sensor 420 senses the ambient light after hatch 410 has been closed and hatch 410 is optionally, transparent or translucent; or includes one or more apertures that allow the transmission of light to sensor 422.

Alternatively, medication is weighed in each compartment 432 as is taught in U.S. Pat. No. 5,042,685 (Moulding, Jr., et al), the entirety of which is hereby incorporated by reference as if fully set forth herein; an embodiment of which is seen in FIG. 6A which shows sensor 422 comprising a weighing platform 440 that is sensitive to the weight of medication 450.

Upon removal of medication 450, as seen in FIG. 6B, weighing platform 440 moves upward in a direction 426, indicating that compartment 432 has been emptied.

As shown, compartments 432 are about 25 millimeters on each of the X and Y axes. In alternative embodiments, compartments 432 are at least about 10 millimeters, 15 millimeters, or at least about 20 millimeters on the X and Y axes. In further embodiments, compartments are no more than about 30 millimeters, 40 millimeters, or even 50 millimeters on the X and Y axes. Additionally, compartments 432 may have different measurements along the X axis than along the Y axis, forming a substantially rectangular shape.

In further embodiments, compartments 432 have varied shaped, for example circular, triangular and/or polygonal, wherein the polygons have more than four sides, for example hexagonal shapes.

As shown, compartments are approximately 25 millimeters deep, on the Z axis. In alternative embodiments, compartments 432 are at least about 10 millimeters, 15 millimeters, or at least about 20 millimeters deep on the Z axis. In further embodiments, compartments are no more than about 30 millimeters, 40 millimeters, or even 50 millimeters deep on Z axis.

The many configurations of compartments 432 in terms of amount, size, and shape are readily understood by those familiar with the art.

In embodiments, at least a portion of box 412, and/or base unit 420 comprise a material selected from the group consisting of: polyethylene, polyvinyl chloride, polyurethane, nylon and a biocompatible polymer fiber.

In embodiments, at least a portion of box 412, and/or base unit 420 comprise a material selected from the group consisting of: metals, synthetic biostable polymer, a natural polymer, and an inorganic material. In embodiments, the biostable polymer comprises a material from the group consisting of: a polyolefin, a polyurethane, a fluorinated polyolefin, a chlorinated polyolefin, a polyamide, an acrylate polymer, an acrylamide polymer, a vinyl polymer, a polyacetal, a polycarbonate, a polyether, a polyester, an aromatic polyester, a polysulfone, and a silicone rubber.

In embodiments, the natural polymer comprises a material from the group consisting of: a polyolefin, a polyurethane, a Mylar, a silicone, and a fluorinated polyolefin.

The many materials from which box 412, and/or base unit 420 may be constructed are readily understood by those familiar with the art.

System 600

Figure 7:
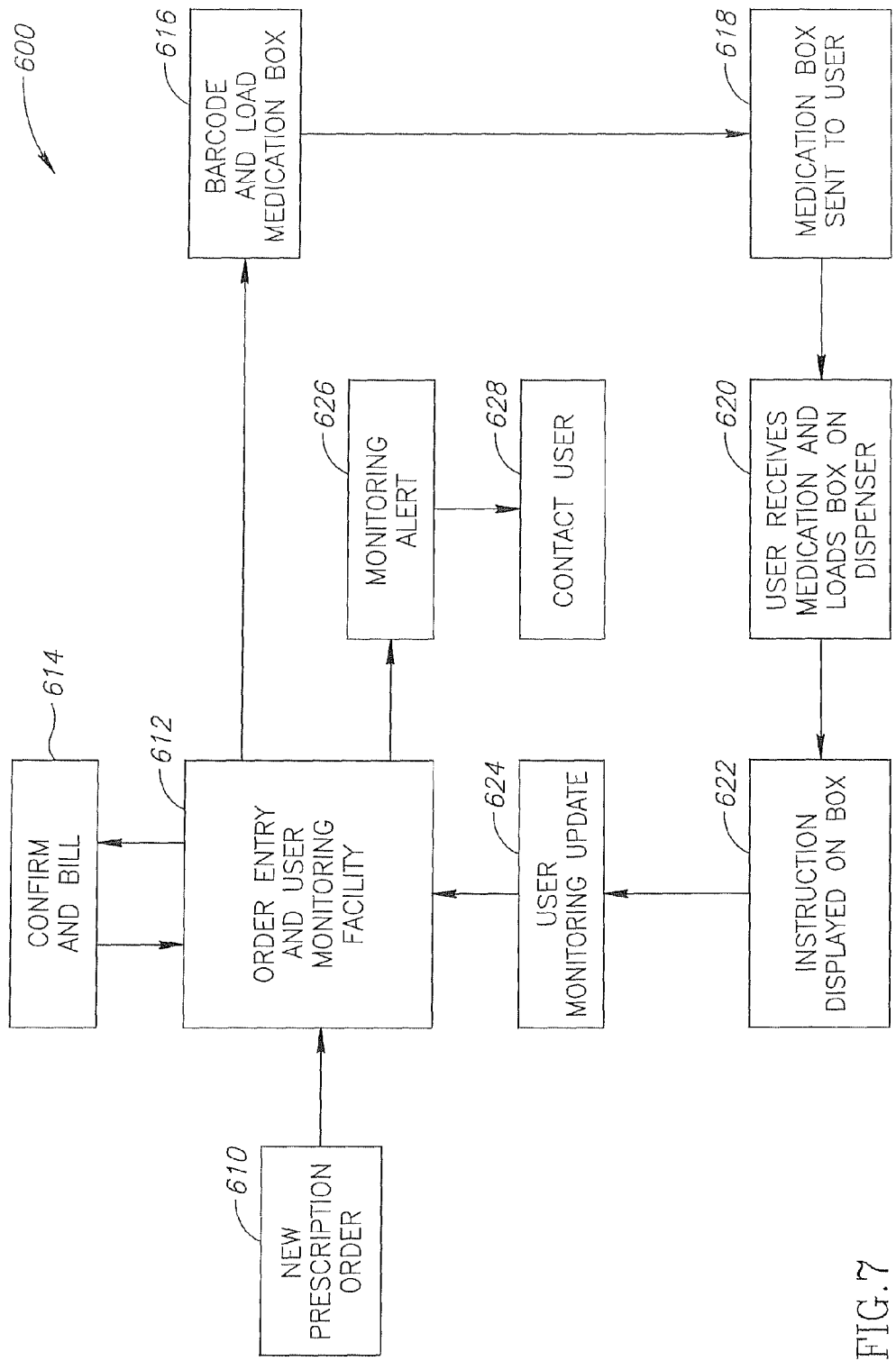

FIG. 7 shows a flowchart of a system 500 for use of disposable medication dispensing system 400 (FIGS. 4-6B). At a new prescription order stage 610, a caregiver, for example a doctor, writes prescriptions for an end user and sends the prescription to a central dispensing station. At an order entry stage 612, the central station record the prescription in a data bank and, at a confirm and bill stage 614, the central station confirms that end user is eligible for receiving the medication, an example of which is taught in U.S. Pat. No. 6,088,429 (Garcia), the entirety of which is hereby incorporated by reference as if fully set forth herein.

Optionally, at bill stage 614, a $3^{rd}$ party payer is billed for the medications, such $3^{rd}$ party payers including, inter alia, an insurance company and/or a welfare agency, for example Medicare in the United States. An example of an embodiment of an electronic billing system that bills directly for dispensed medications is taught in U.S. Pat. No. 6,757,898 (Ilsen, et al), the entirety of which is hereby incorporated by reference as if fully set forth herein.

The central station then sends the prescription to a loading stage 616 where the medication is loaded into a disposable medication box, for example box 420 seen in FIG. 4. In embodiments, loading stage 616 includes electronically mechanized loading systems, for example pill loading robots, that load and package medication, and example of which is taught in U.S. Pat. No. 5,522,525 (McLaughlin, et al), the entirety of which is hereby incorporated by reference as if fully set forth herein.

Additionally, the central station encodes medication dispensing information is on bar code 414 to be displayed on display 424.

Returning to FIG. 7, at a send stage 618, the central dispensing station sends the medication box to the end user. At a receive stages 620, the end user or a caregiver, for example a visiting nurse, loads disposable medication box 412 (FIG. 4) on base unit 420 and base unit reads bar code 414. At an instruction displayed stage 622 the end user is notified of proper times to take medication and, upon taking medication, a user monitoring stage 624 provides an update to the central station.

Communication provided at monitoring stage 624 optionally uses a wireless transponder noted above. Alternatively, communication is transmitted through a hardwire hookup to a telephone line. In still other embodiments, communication occurs through a hardwire hookup to a computer that transmits via the internet; the many ways of communicating medication updates being well known to those familiar with the art.

In the event that the information from user monitoring phase 624 indicates a failure to take medication, the central station proceeds to a monitoring alert stage 626 wherein the end user is contact verbally, for example telephonically. In the event that the end user does not respond to the verbal contact, the central station proceeds to a contact user stage 628 wherein physical contact, via a monitoring counselor, is made with the end user.

RFID Medication Dispenser

Figure 8:
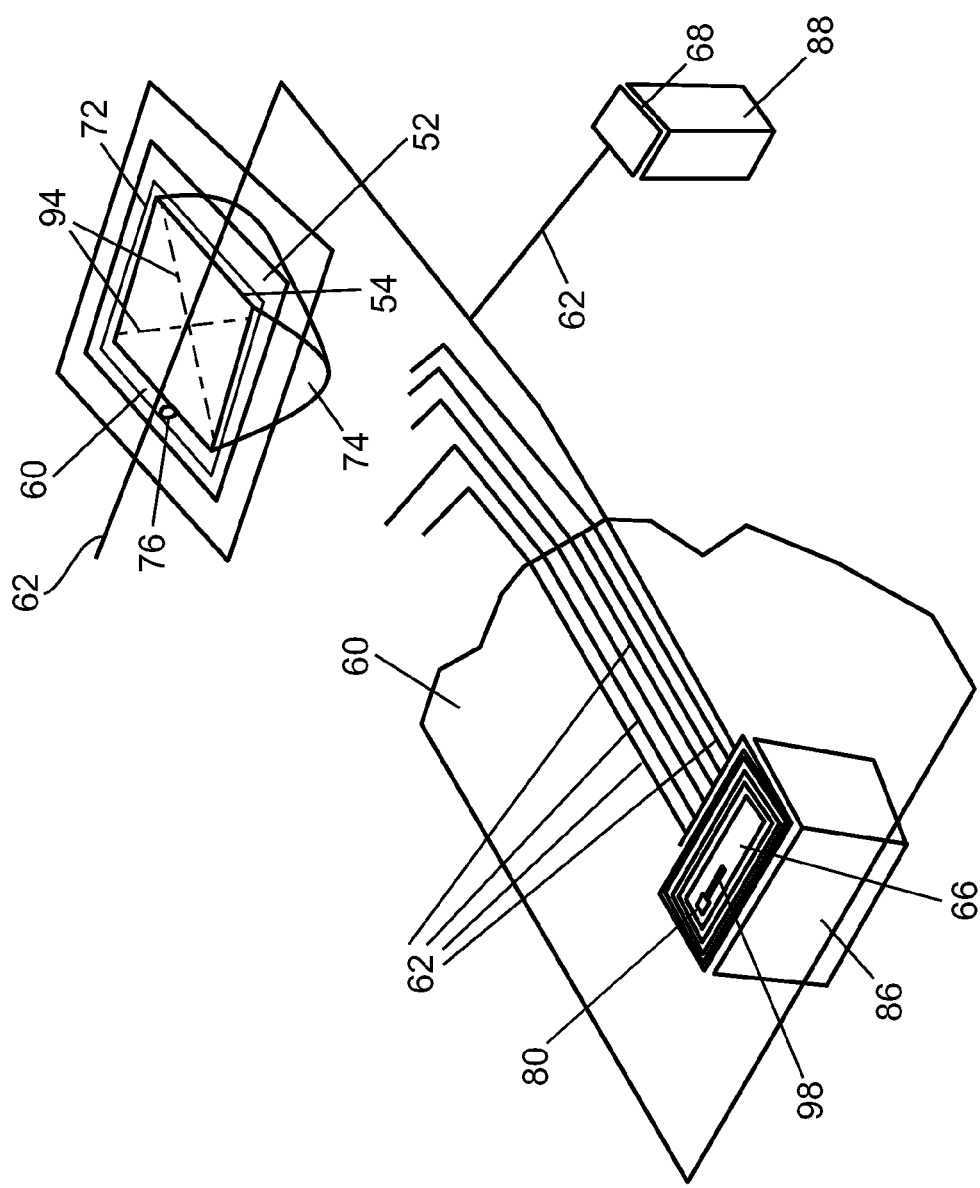

FIG. 8 shows a schematic diagram of an RFID transponder tag 66 that signals signal opening of a medication container 74.

RFID transponder tag 66 includes an integrated circuit chip 80 and an antenna 98 connected to integrated circuit chip 80. A perforation 94 is broken as the user breaks through a covering layer 52 and a substrate layer 60 to take medications contained within medication container 74 according to a predetermined schedule. When substrate layer 60 is broken, a conductor strip 62 is broken so that the current supplied by a RFID power supply 88 to a current terminal 68 is interrupted from medication container 74. When RFID power supply 88 activates, the interruption is registered on integrated circuit chip 80.

When an RFID interrogator 86 transmits a coded RF signal, the incident RF reflects off RFID transponder tag 66, including the encoding information stored in the memory of the integrated circuit chip 80. RFID interrogator 86 is apprised by integrated circuit chip 80 that medication container 74 has been opened. The central station, described above, receives the encoded information from RFID transponder tag 66 via one or more of the wired and wireless transmission systems noted above, and is apprised that the user has likely consumed the medication contained therein.

Alternatively, when conductor strip 64 remains unbroken, the current supplied by RFID power supply 88 remains uninterrupted from medication container 74. The failure to interrupt conductor strip 64 remains registered on integrated circuit chip 80 when RFID power supply 88 activates. Following a pre-set period of time following the scheduled opening of medication container 74 by the user, RFID interrogator 86 sends a signal to RFID transponder tag 66 and the reflected RF indicates to the RFID interrogator 86 that medication container 74 is intact. In such cases, the central station is apprised that the user has failed to consume the medication.

In embodiments, RFID transponder tag 66 is a passive device, requiring no RFID power and instead deriving power from the RF signal used to interrogate RFID transponder tag 66. RFID transponder tag 66 is commercially available from suppliers such as, for example, Texas Instruments. As will be appreciated by a person skilled in the art, commercial transponders are typically fabricated and supplied with the integrated circuit chip 80 and antenna 98 on substrate layer 60 comprising, for example, a polyester or a polyimide.

It will be appreciated that perforation 94 need not take the form of interrupted cuts, but may be formed in any suitable manner such as, for example, scoring covering layer 52 and substrate layer 60 covering layer 52. In whichever manner the line of weakness is created, the essential requirement is that substrate layer 60 and covering layer 52 are easily torn, thereby severing conductor 64 which leads to RFID transponder tag 66.

In embodiments, covering layer 52 provides protective strength to prevent damage during handling to RFID transponder tag 66. Covering layer 52 may comprise, for example paper or a polymer material such as PVC.

RFID transponder tag 66, integrated circuit chip 80, antenna 98 and conductor 64 may be assembled in between substrate layer 60 and covering layer 52 during any one of a number of lamination processes that are well-known to those familiar with the art.

Figure 9:
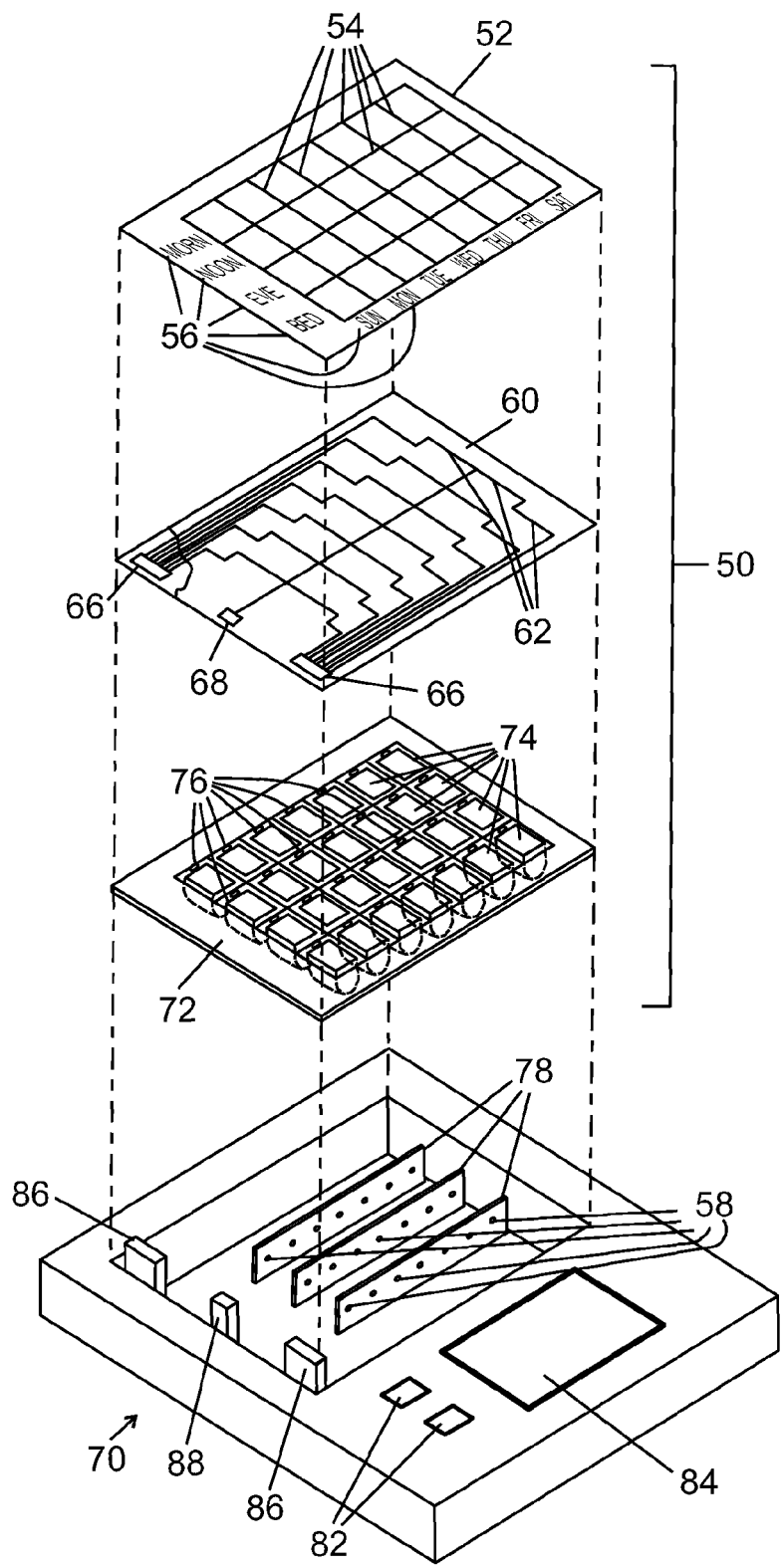

As shown in FIG. 9, when assembled, a disposable medication packet 50 including multiple medication containers 74 is removably set into a dispenser base 70 which includes RFID interrogators 86 that communicate with RFID transponder tags 66, as noted above.

Optionally, covering layer 52 optionally includes markings 54 around medication compartments and scheduling markers 56, for example "morning noon and/or night" and/or the days of the week. The underside of substrate layer 60 is coated with a suitable adhesive formed into a pattern to attach substrate layer 60 to medication container 72.

Optionally, dispenser base 70 includes buttons 82 that are used by the user, for example, to alert the central station of a home emergency, for example an untoward reaction to a medication.

Dispenser base 70 includes, for example, LED strips 78 having LEDs 58 that light up according to a preset schedule and shine through apertures 76 in substrate layer 60 and covering layer 52. The lighting of an LED 58 signals the user to take medication contained in a given medication compartment 74. In conjunction with the lighting of LED 58 a readout 84 optionally apprises the user as to how to take the medication, for example "take with food" appearing on readout 84.

It is expected that during the life of a patent maturing from this application, many relevant configurations of medicine dispensing systems and sensor systems will be developed and the scope of the terms "medicine dispensing system" and "sensor" is intended to include all such new technologies a priori.

As used herein the term "about" refers to ±10%.

The terms "comprises", "comprising", "includes", "including", "having" and their conjugates, mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

The invention claimed is:

1. A medication dispensing system, comprising:
   a container including at least two compartments, each said compartment including:
      a cavity configured to contain at least one medication;
      a covering layer and a substrate layer over said cavity, wherein both said layers are configured to break under pressure;
   an interrogator-readable RFID circuit operatively connected to said container via said substrate layer, and communicable with at least one RFID circuit interrogator;
   and
   a dispenser base configured for including said at least one RFID circuit interrogator.

2. The system of claim 1, wherein said covering layer and said substrate layer are configured with a perforation breakable under said pressure.

3. The system of claim 1, wherein said covering layer and said substrate layer are configured to break according to a schedule.

4. The system of claim 1, wherein said covering layer includes markings or/and schedule markers around said container.

5. The system of claim 1, wherein underside of said substrate layer is coated with an adhesive formed into a pattern to attach said substrate layer to said container.

6. The system of claim 1, further including a conductive element operatively connected to each of said at least two compartments and to said interrogator-readable RFID circuit.

7. The system of claim 6, wherein said conductive element is configured in between said covering layer and said substrate layer, and is configured to sever upon breaking said substrate layer.

8. The system of claim 6, further including a current terminal operatively connected to said conductive element and to said interrogator-readable RFID circuit, wherein current is supplied to said current terminal from an RFID power supply for activating said interrogator-readable RFID circuit.

9. The system of claim 1, wherein said interrogator-readable RFID circuit includes at least one RFID transponder tag with each including an integrated circuit chip and an antenna connected to said integrated circuit chip.

10. The system of claim 1, wherein said interrogator-readable RFID circuit is communicable with a remote location via a wired or/and wireless transmission system.

11. The system of claim 1, wherein said container, including said at least two compartments, is removably set into said dispenser base.

12. The system of claim 11, wherein said dispenser base includes light-emitting diode strips having light-emitting diodes configured for lighting up according to a preset medication schedule.

13. The system of claim 12, wherein said light-emitting diodes shine through apertures in said substrate layer and said covering layer of said at least two compartments.

14. A medical object dispensing system, comprising:
a container including at least two compartments, each said compartment including:
a cavity configured to contain at least one medical object;
a covering layer and a substrate layer over said cavity, wherein both said layers are configured to break under pressure;
an interrogator-readable RFID circuit operatively connected to said container via said substrate layer, and communicable with at least one RFID circuit interrogator;
and
a dispenser base configured for including said at least one RFID circuit interrogator.

15. A device for dispensing medication, the device comprising:
a container including at least two compartments, each said compartment including:
a cavity configured to contain at least one medication;
a covering layer and a substrate layer over said cavity, wherein both said layers are configured to break under pressure; and
a conductive element in between said covering layer and said substrate layer, and configured to sever upon breaking said substrate layer;
a dispenser base, wherein said container, including said at least two compartments, is removably set into said dispenser base;
said dispenser base includes light-emitting diode strips having light-emitting diodes configured for lighting up according to a preset medication schedule; and
said dispenser base includes light-emitting diode strips having light-emitting diodes configured for lighting up according to a preset medication schedule.

16. The device of claim 15, wherein said covering layer and said substrate layer are configured with a perforation breakable under said pressure.

17. The device of claim 15, wherein said covering layer and said substrate layer are configured to break according to a schedule.

18. The device of claim 15, wherein said covering layer includes markings or/and schedule markers around said container.

19. The device of claim 15, wherein underside of said substrate layer is coated with an adhesive formed into a pattern to attach said substrate layer to said container.

20. The device of claim 15, further including an interrogator-readable RFID circuit operatively connected to said container.

21. The device of claim 20, wherein said operative connection is via said substrate layer.

22. The device of claim 20, further including a current terminal operatively connected to said conductive element and to said interrogator-readable RFID circuit, wherein current is supplied to said current terminal from an RFID power supply for activating said interrogator-readable RFID circuit.

23. The device of claim 20, wherein said interrogator-readable RFID circuit includes at least one RFID transponder tag with each including an integrated circuit chip and an antenna connected to said integrated circuit chip.

24. The device of claim 20, wherein said interrogator-readable RFID circuit is communicable with a remote location via a wired or/and wireless transmission system.

25. The device of claim 20, wherein said interrogator-readable RFID circuit is communicable with at least one RFID circuit interrogator.

26. A device for dispensing medical objects, the device comprising:
a container including at least two compartments, each said compartment including:
a cavity configured to contain at least one medical object;
a covering layer and a substrate layer over said cavity, wherein both said layers are configured to break under pressure;
a conductive element in between said covering layer and said substrate layer, and configured to sever upon breaking said substrate layer;
a dispenser base, wherein said container, including said at least two compartments, is removably set into said dispenser base;
said dispenser base includes light-emitting diode strips having light-emitting diodes configured for lighting up according to a preset medication schedule; and
said dispenser base includes light-emitting diode strips having light-emitting diodes configured for lighting up according to a preset medication schedule.

27. A medication dispensing system, comprising:
a container including at least two compartments, each said compartment including:
a cavity configured to contain at least one medication;
a covering layer and a substrate layer over said cavity, wherein both said layers are configured to break under pressure;
an interrogator-readable RFID circuit operatively connected to said container via said substrate layer;

a dispenser base, wherein said container, including said at least two compartments, is removably set into said dispenser base;

said dispenser base includes light-emitting diode strips having light-emitting diodes configured for lighting up according to a preset medication schedule; and said dispenser base includes light-emitting diode strips having light-emitting diodes configured for lighting up according to a preset medication schedule.

28. The system of claim 27, wherein said covering layer and said substrate layer are configured with a perforation breakable under said pressure.

29. The system of claim 27, wherein said covering layer and said substrate layer are configured to break according to a schedule.

30. The system of claim 27, wherein said covering layer includes markings or/and schedule markers around said container.

31. The system of claim 27, wherein underside of said substrate layer is coated with an adhesive formed into a pattern to attach said substrate layer to said container.

32. The system of claim 27, further including a conductive element operatively connected to each of said at least two compartments and to said interrogator-readable RFID circuit.

33. The system of claim 32, wherein said conductive element is configured in between said covering layer and said substrate layer, and is configured to sever upon breaking said substrate layer.

34. The system of claim 32, further including a current terminal operatively connected to said conductive element and to said interrogator-readable RFID circuit, wherein current is supplied to said current terminal from an RFID power supply for activating said interrogator-readable RFID circuit.

35. The system of claim 27, wherein said interrogator-readable RFID circuit includes at least one RFID transponder tag with each including an integrated circuit chip and an antenna connected to said integrated circuit chip.

36. The system of claim 27, wherein said interrogator-readable RFID circuit is communicable with a remote location via a wired or/and wireless transmission system.

37. The system of claim 27, wherein said interrogator-readable RFID circuit is communicable with at least one RFID circuit interrogator.

38. The system of claim 37, wherein said dispenser base is configured for including said at least one RFID circuit interrogator.

39. The system of claim 38, wherein said light-emitting diodes shine through apertures in said substrate layer and said covering layer of said at least two compartments.

40. A medical object dispensing system, comprising:

a container including at least two compartments, each said compartment including:

a cavity configured to contain at least one medical object;

a covering layer and a substrate layer over said cavity, wherein both said layers are configured to break under pressure;

an interrogator-readable RFID circuit operatively connected to said container via said substrate layer;

a dispenser base, wherein said container, including said at least two compartments, is removably set into said dispenser base;

said dispenser base includes light-emitting diode strips having light-emitting diodes configured for lighting up according to a preset medication schedule; and said dispenser base includes light-emitting diode strips having light-emitting diodes configured for lighting up according to a preset medication schedule.

* * * * *